US00PP31143P2

(12) United States Plant Patent
Kerley et al.

(10) Patent No.: US PP31,143 P2
(45) Date of Patent: Nov. 26, 2019

(54) ***PRIMULA VULGARIS* 'KERBELGOLDIE'**

(50) Latin Name: *Primula vulgaris*
Varietal Denomination: KERBELGOLDIE

(71) Applicants: Priscilla Kerley, Cambridge (GB); David Kerley, Cambridge (GB); Sarah Kerley, Cambridge (GB); Timothy Kerley, Cambridge (GB)

(72) Inventors: Priscilla Kerley, Cambridge (GB); David Kerley, Cambridge (GB); Sarah Kerley, Cambridge (GB); Timothy Kerley, Cambridge (GB)

( * ) Notice: Subject to any disclaimer, the term of this patent is extended or adjusted under 35 U.S.C. 154(b) by 0 days.

(21) Appl. No.: 15/998,358

(22) Filed: Aug. 7, 2018

(30) Foreign Application Priority Data

Jul. 27, 2018 (QZ) ..... PBR 201802453

(51) Int. Cl.
*A01H 5/02* (2018.01)

(52) U.S. Cl.
USPC ..... Plt./472

(58) Field of Classification Search
USPC ..... Plt./472
See application file for complete search history.

*Primary Examiner* — Annette H Para
(74) *Attorney, Agent, or Firm* — Cassandra Bright

(57) ABSTRACT

A new and distinct *Primula vulgaris* cultivar named 'KERBELGOLDIE' is disclosed, characterized by deep golden-yellow, large double flowers, with enlarged sepals, strong peduncles, and early flowering. Plants have shown the ability to be propagated by tissue culture at a good rate. The new variety is a *Primula vulgaris*, suitable for outdoor landscape and container use.

2 Drawing Sheets

Figure 1:
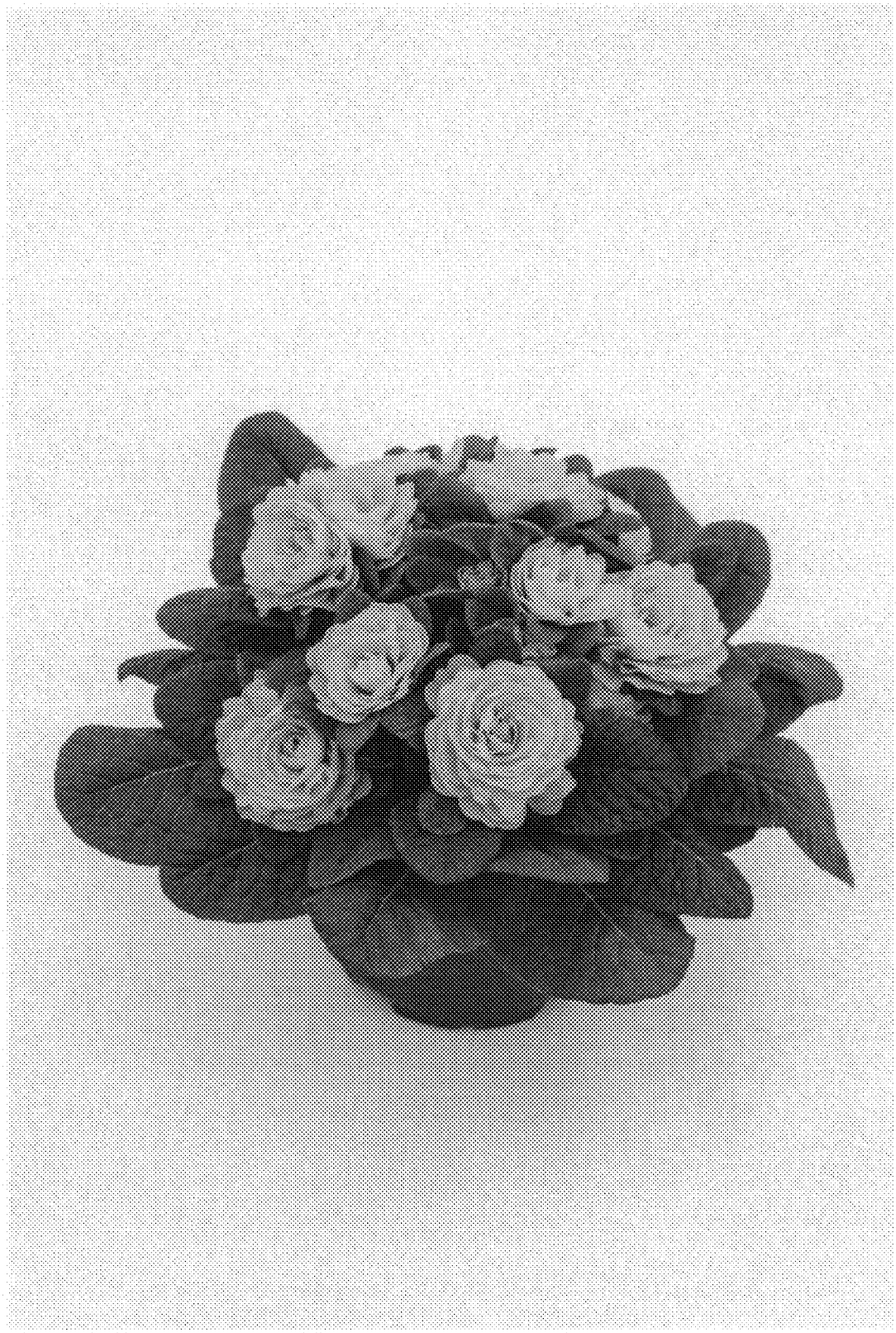

Latin name of the genus and species: *Primula vulgaris.*
Variety denomination: 'KERBELGOLDIE'.

BACKGROUND OF THE INVENTION

The new cultivar is the product of a planned breeding program under the direction of the inventors, David Kerley, Priscilla Kerley, Sarah Kerley, and Timothy Kerley, all citizens of the United Kingdom. The objective of the breeding program was to produce new, compact pot-type *Primula vulgaris* cultivars with abundant double flowers for commercial ornamental purposes. The new cultivar resulted from crossing of the seed parent, the unpatented, proprietary variety *Primula vulgaris* '10-462-1', and the pollen parent, the unpatented, proprietary variety *Primula vulgaris* '10-462-9'. The selection of the new variety 'Kerbelgoldie' was made in February 2011, by the inventors at a research greenhouse located in Cambridge, UK.

Asexual reproduction of the new cultivar 'KERBELGOLDIE' by division was first performed at the same research greenhouse in Cambridge, UK during September of 2011, by division and tissue culture. Both methods have shown that the unique features of this cultivar are stable and reproduced true to type in successive generations.

SUMMARY OF THE INVENTION

The cultivar 'KERBELGOLDIE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBELGOLDIE' These characteristics in combination distinguish 'KERBELGOLDIE' as a new and distinct *Primula* cultivar:

1. Golden yellow flowers (no other double *Primula vulgaris* with this color to the best of our knowledge).
2. Early flowering.
3. Enlarged sepals behind the flower.
4. Double flowers.
5. Large flowers.
6. Strong peduncles.
7. Good propagation rate in tissue culture.
8. Very fragrant.

PARENT COMPARISON

Plants of the new cultivar 'KERBELGOLDIE' are similar to plants of the seed parent, proprietary seedling '10-462-1', in most horticultural characteristics. However, plants of the new cultivar differ in the following ways:

1. New cultivar has double flowers; seed parent is single flowered.
2. New variety is sterile; seed parent is fertile.
3. Flowers of new variety are long lasting; seed parent's flowers do not last as long.
4. New cultivar has a long flowering period; parent ceased flowering when seed had set.

Plants of the new cultivar 'KERBELGOLDIE' are similar to plants of the pollen parent, proprietary seedling '10-462-9', in most horticultural characteristics. However, plants of the new cultivar differ in the following ways:

1. New cultivar has double flowers; pollen parent is single flowered.
2. New variety is sterile; seed parent is fertile.
3. Flowers of new variety are long lasting; pollen parent's flowers do not last as long.

4. New cultivar has a long flowering period; parent ceased flowering when seed had set under natural conditions.

COMMERCIAL COMPARISON

Plants of the new variety can be compared to plants of the *Primula vulgaris* cultivar 'Kerbelbut' (U.S. Plant Pat. No. 16,373). In side-by-side comparisons conducted in Over, Cambridge, United Kingdom, plants of the new *Primula* differed from plants of the cultivar 'Kerbelbut' in the following characteristics:

1. New variety's mature flower is color 12A on the upper surface, 9B and C on the lower surface; comparator's color is 6A.
2. New cultivar's flower diameter is 5 cm; comparator's diameter is 4 cm.
3. Flowering time for new variety is about 2 weeks earlier than that of comparator, depending on climate.

Plants of the 'KERBELGOLDIE' can be compared to plants of the *Primula vulgaris* cultivar 'Sunshine Susie', not patented. In side-by-side comparisons conducted in Over, Cambridge, United Kingdom, plants of the new *Primula* differed from plants of the cultivar 'Sunshine Susie' in the following characteristics:

1. Flower color of new cultivar is a golden yellow; comparator is a soft yellow.
2. New cultivar's flower size is large; comparator's is small to medium.
3. New variety has an enlarged calyx—jack in the green; comparator has a normal calyx.
4. New variety has a short, stiff peduncle; comparator has a medium-long, thin peduncle.

BRIEF DESCRIPTION OF THE PHOTOGRAPHS

The accompanying photograph in FIG. 1 illustrates in full color typical plants of 'KERBELGOLDIE' grown in Over, Cambridge, United Kingdom, in a glass-covered greenhouse and under commercial production practices during the spring. Plants were about four to five months old when the photographs were taken. During the production of the plants, day temperatures ranged from 5 to 15 degrees C. and night temperatures ranged from 2 to 12 degrees C.

Figure 2:
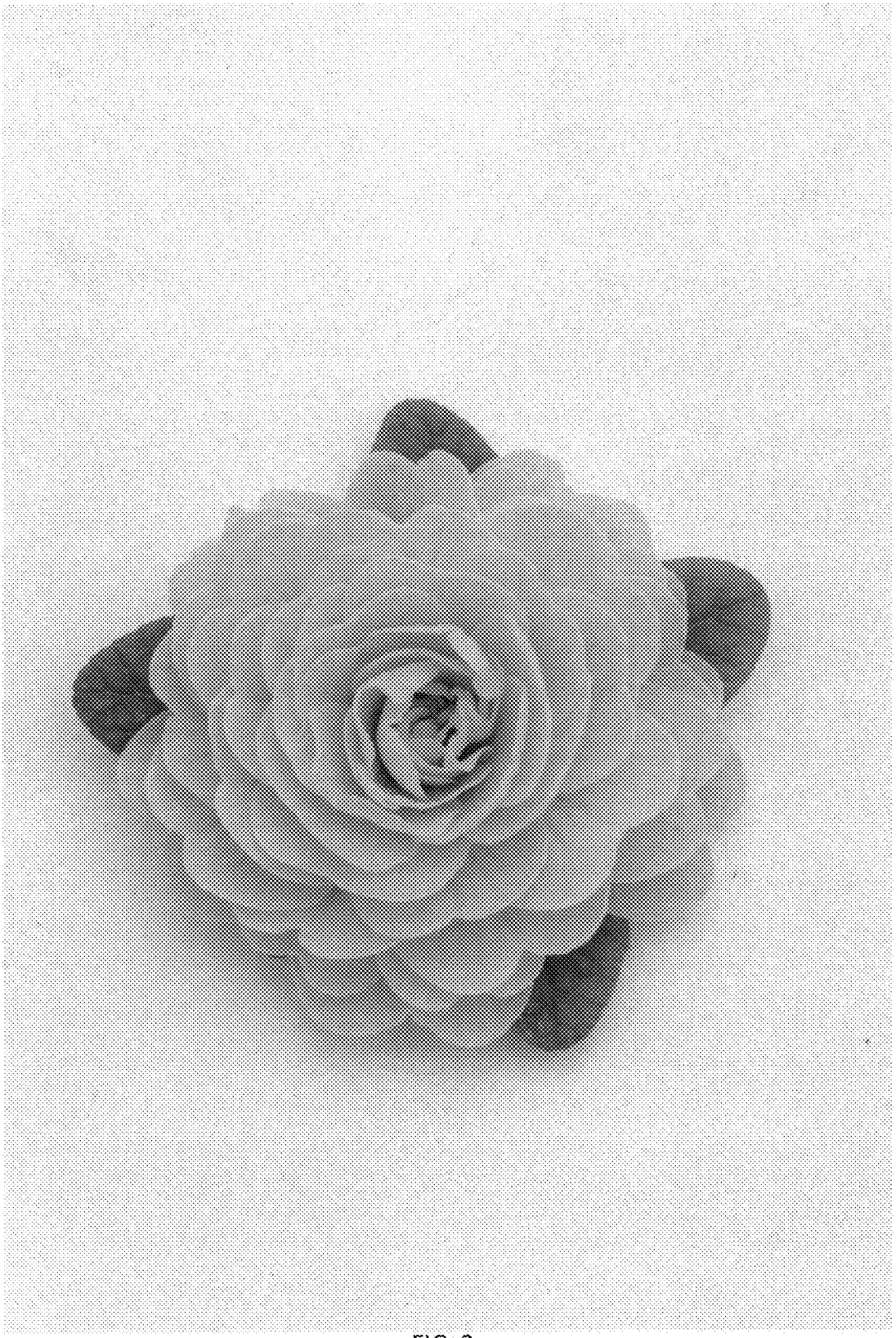

FIG. 2 illustrates a close up of a typical flower of 'KERBELGOLDIE'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 1995 except where general terms of ordinary dictionary significance are used. The following observations and measurements describe 'KERBELGOLDIE' plants grown under commercial production practices during the spring in Cambridge, United Kingdom. During the production of the plants, day temperatures ranged from 5 to 15 degrees C. and night temperatures ranged from 2 to 12 degrees C. No chemical or photoperiodic treatments were given. Measurements and numerical values represent averages of typical flowering types.

Botanical classification: *Primula vulgaris* 'KERBELGOLDIE'.

Age of the plant described: Approximately 4 to 5 months in an 11 cm pot.

PROPAGATION

Method: Tissue culture.

Time to initiate roots: About four weeks at 20° C.

Time to produce a rooted young plant: About six weeks at 20° C.

Root description: Fibrous, colored near RHS White 155A.

PLANT

Growth habit: Upright, compact and uniform; inverted triangle. Vigorous growth.

Height: Approximately 11 to 13 cm.

Plant spread: Approximately 22 to 25 cm.

Branching characteristics: No branches, foliage emerges basally.

FOLIAGE

Leaf:

*Arrangement.*—Basal, simple.

*Average length.*—Approximately 12 cm.

*Average width.*—Approximately 4 to 5 cm.

*Shape of blade.*—Oblanceolate.

*Apex.*—Obtuse.

*Base.*—Acute.

*Margin.*—Slightly crenate, irregular.

*Texture of top surface.*—Smooth, rugose.

*Texture of bottom surface.*—Veins prominent.

*Color.*—Developing foliage upper side: Darker than RHS 144A. Developing foliage under side: Near RHS 144A. Mature foliage upper side: Near RHS 146A. Mature foliage under side: Near RHS 146B.

*Venation.*—Type: Pinnate. Venation color upper side: Near RHS 145B-C. Venation color under side: Near RHS 145C-D.

Petiole:

*Length.*—Approximately 1.0 to 2.5 cm.

*Diameter.*—0.4 to 0.7 cm.

*Color.*—Upper Surface: Near RHS 145D, sometimes tinged 186C towards base of developing leaves. Lower Surface: Near RHS 157A sometimes tinged 186D toward base.

*Texture all surfaces.*—Glabrous, smooth.

FLOWER

Bloom period: Recurrent flowering during the Spring under United Kingdom outdoor conditions. Very free flowering.

Inflorescence: Solitary, rounded double flowers, upright and outwardly facing.

Persistent or self-cleaning: Persistent.

Fragrance: Fragrant.

Flowers per plant: 45-62 flowers and buds.

Flower bud:

*Height.*—1 to 1.3 cm.

*Diameter.*—0.9 to 1.2 cm.

*Shape.*—Ovoid.

*Color.*—RHS 6A.

Individual flower:

*Diameter.*—4 to 5 cm.

*Depth.*—2.5 to 3.3 cm.

*Petals.*—53 to 72 per flower, in several concentric whorls.

*Length* (*including tube*).—1.5 to 2.4 cm.

*Width.*—1.3 to 2.0 cm.

*Shape.*—Obcordate.

*Apex.*—Emarginate.

*Margin.*—Mostly entire.

*Texture, upper and lower surfaces.*—Glabrous, satiny, slightly corrugated lower surface.

*Color.*—Developing petals, upper surface: RHS 6A. Developing petals, lower surface: RHS 6B. Mature petals, upper surface: RHS 12A. Mature petals, Lower surface: RHS 9B and 9C, colors present individually.

*Sepals.*—Quantity per flower: 5 in a single whorl; fused at base; large and "frame" the flower. Length: 3 to 3.5 cm. Width: 1.5 to 2.2 cm. Shape: Oblanceolate. Apex: Obtuse. Texture, upper and lower surfaces: Smooth, slightly rugose. Color, upper surface: RHS 146A. Color, lower surface: RHS 146B-C.

Peduncle:

*Peduncle length.*—8.5 to 12 cm.

*Peduncle diameter.*—0.2 to 0.3 cm.

*Orientation.*—Mostly erect.

*Strength.*—Strong.

*Color.*—Near RHS 160C, streaked 186B to a greater or lesser extent.

*Texture.*—Pubescent.

REPRODUCTIVE ORGANS

Development of reproductive organs has not been observed.

OTHER CHARACTERISTICS

Disease resistance: Plants of the new *Primula* have not been noted to be resistant to pathogens and pests common to *Primula.*

Temperature tolerance: Plants of the new *Primula* have been observed to have tolerated temperatures from about −5 to 28 degrees C.

Fruit/seed production: Fruit and seed production not observed, flowers are sterile.

What is claimed is:

1. A new and distinct cultivar of *Primula* plant named 'KERBELGOLDIE' as herein illustrated and described.

* * * * *